(12) United States Patent
Li et al.

(10) Patent No.: US 8,481,318 B2
(45) Date of Patent: *Jul. 9, 2013

(54) NESTIN-EXPRESSING HAIR FOLLICLE STEM CELLS

(75) Inventors: Lingna Li, San Diego, CA (US); Meng Yang, San Diego, CA (US)

(73) Assignee: Anticancer, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/694,213

(22) Filed: Jan. 26, 2010

(65) Prior Publication Data

US 2010/0159589 A1    Jun. 24, 2010

Related U.S. Application Data

(63) Continuation of application No. 10/251,657, filed on Sep. 20, 2002, now Pat. No. 7,666,675.

(60) Provisional application No. 60/323,963, filed on Sep. 20, 2001.

(51) Int. Cl.
*C12N 5/00* (2006.01)
*C12N 5/02* (2006.01)
*C12N 5/06* (2006.01)
*C12N 5/08* (2006.01)

(52) U.S. Cl.
USPC ............ 435/378; 435/325; 435/354; 435/366

(58) Field of Classification Search
USPC .................................. 435/325, 354, 366, 378
See application file for complete search history.

(56) References Cited

FOREIGN PATENT DOCUMENTS

| WO | WO-95/01423 | 1/1995 |
|----|-------------|--------|
| WO | WO-02/40645 | 5/2002 |

OTHER PUBLICATIONS

Ma et al., 2004, Ann Acad Med Singapore, vol. 33, p. 784-788.*
Abeyta et al., Human Molecular Genetics (2004) 13(6):601-608.
Akiyama et al., Journal of Investigative Dermatology (2000) 114(2):321-327.
Allegrucci et al., Human Reproduction Update (2006) Vol: Advance Access published on Aug. 26, 2006, pp. 1-18.
Amoh et al., Proceedings of the National Academy of Sciences USA (2004) 101(36):13291-13295.
Andressen et al., Stem Cells (2001) 19:419-424.
Bickenbach et al., Advances in Dermatology (2000) 16:159-183.
Cotsarelis et al., Cell (1990) 61:1329-1337.
Cotsarelis, The Journal of Clinical Investigation (2006) 116(1):19-22.
Houdebine, Journal of Biotechnology (2002) 98:145-160.
Kabayashi et al., PNAS USA (1993) 90:7391-7395.
Kawaguchi et al., Mol. Cell Neurosci. (2001) 17:259-273.
Kappel et al., Current Opinion in Biotechnology (1992) 3:548-553.
Lako et al., Development Growth and Differentiation (2001) 43:S22.
Lako et al., Journal of Cell Science (2002) 115(20):3967-3974.
Li et al., Proceedings of the National Academy of Sciences USA (2003) 100(17):9958-9961.
Lyle et al., Journal of Investigative Dermatology, Symposium Proceedings/The Society for Investigative Dermatology (1999) 4(3):296-301.
Lyle et al., Journal of Science (1998) 111(21):3179-3188.
Mokry and Nemecek, Acta Medica—Hradec Kralove (1998) 41(2):73-80.
Oshima et al., Cell (2001) 104:233-245.
Rao, Developmental Biology (2004) 275:269-286.
Reynolds et al., Journal of Cell Science (1991) 99:373-385.
Roy et al., Nature Medicine (2000) 6(3):271-277.
Sato et al., Developmental Biology (2003) 260:404-413.
Sawamoto et al., Journal of Neuroscience (2001) 21(11):3895-3903.
Sigmund, Arterioscler. Thromb. Vasc. Biol. (2000) pp. 1425-1429.
Supplementary European Search Report for EP 02 77 3519, mailed on Oct. 19, 2004, 5 pages.
Tani et al., Proceedings of the National Academy of Sciences USA (2000) 97(20):10960-10965.
Taylor et al., Cell (2000) 102:451-461.
Toma et al., Nature Cell Biology (2001) 3:778-784.
Turksen, Developmental Cell (2004) 6(4):454-456.
Yu et al., American Journal of Pathology (2006) 168(6):1-6.
Amoh et al., "Human and mouse hair follicles contain both multipotent and monopotent stem cells", Cell Cycle (2009) 8(1):176-177.
Amoh et al., "Human Hair Follicle Pluripotent Stem (hfPS) Cells Promote Regeneration of Peripheral-Nerve Injury: An Advantageous Alternative to ES and iPS Cells", Journal of Cellular Biochemistry (2009) 107:1016-1020.
Tiede et al., "Hair follicle stem cells: Walking the maze", European Journal of Cell Biology (2007) 86:355-376.

* cited by examiner

*Primary Examiner* — Shin-Lin Chen
(74) *Attorney, Agent, or Firm* — Morrison & Foerster LLP

(57) ABSTRACT

Hair follicle stem cells are isolated in a method which relies on the identification of stem cells as being small, spindle, oval or round shaped nestin-expressing cells that are located in the permanent upper part of telogen hair follicles below the sebaceous glands and in the bulge area.

3 Claims, 3 Drawing Sheets

NESTIN-EXPRESSING HAIR FOLLICLE STEM CELLS

CROSS-REFERENCE TO RELATED APPLICATIONS

This application is a continuation of U.S. Ser. No. 10/251,657 filed 20 Sep. 2002, which claims benefit under 35 U.S.C. §119(e) from provisional application Ser. No. 60/323,963 filed 20 Sep. 2001, the contents of which are incorporated herein by reference.

TECHNICAL FIELD

The invention relates to hair follicle stem cells and their uses. Specifically, the invention is directed to nestin-expressing hair follicle stem cells, methods of isolating the stem cells and methods of treating diseases or disorders using the stem cells.

BACKGROUND ART

Although the importance of stem cell therapy is recognized, stem cell therapy remains controversial due to the use of embryonic stem cells used for such therapy. Also, stem cells from sources such as bone marrow are difficult to harvest. It would be beneficial to the field if there was a readily accessible source of adult stem cells for harvesting which could impart the same benefits as more controversial and less accessible sources of stem cells. The invention has addressed such a need by the discovery of stem cells that are derived from mammalian hair follicles. A brief background relating to hair provides the basis for hair follicle stem cells of the invention.

Hair growth is a unique cyclic regeneration phenomenon. The hair follicle undergoes repeated cycles of periods of growth (anagen), regression (catagen) and rest (telogen) throughout the life of mammals. The location and function of hair follicular stem cells is a crucial issue for understanding both biology and pathology of hair growth (Oshima, H., et al., *Cell* (2001) 104:233-245). Label-retaining cells, a characteristic of stem cells, were found to reside in the permanent upper portion of hair follicle, the so-called the bulge area (Cotsarelis, G., et al., *Cell* (1990) 61:1329-1337).

Recently Taylor, G., et al. (*Cell* (2000) 102:451-461), reported that hair follicle bulge stem cells are potentially bipotent as they can give rise to not only the hair follicle, but also the epidermis. Other experiments (Oshima, et al., (supra)) also have provided new evidence that the upper outer root sheath of vibrissal follicles of adult mice contains multipotent stem cells, which can differentiate to hair follicle matrix cells, sebaceous gland basal cells and epidermis. Most recently, Toma, J. G., et al. (*Nature Cell Biology* (2001) 3:778-784), reported that multipotent adult stem cells isolated from mammalian skin dermis, named skin derived precursors (SKPs), can proliferate and differentiate in culture to produce neurons, glia, smooth muscle cells, and adipocytes. However, the exact location of these stem cells in skin and their function were unclear.

It would be useful to the field to isolate stem cells from hair that are related to neural stem cells. According to the invention, a relationship of hair follicle stem cells and neural stem cells has been made.

DISCLOSURE OF THE INVENTION

The invention is directed to isolated hair follicle stem cells and cells differentiated therefrom. Preferably, the cells are isolated based on a marker, such as nestin, and more preferably, nestin linked to green fluorescent protein.

Another aspect of the invention is directed to a method of isolating hair follicle stem cells comprising providing skin containing hair follicles from a mammal and isolating the hair follicle stem cells therefrom. Preferably, the skin is telogen skin.

In another aspect of the invention, the isolated hair follicle stem cells are further cultured in culture media to produce differentiated cells. In a preferred embodiment, the culture medium comprises FBS, BDNF, PDGF or CNTF. In a further preferred embodiment, the differentiated cells are neurons, astrocytes, smooth muscle cells, or adipocytes.

Another aspect of the invention is directed to a method of treating a disorder, preferably a neurological or degenerative disorder, comprising implanting the stem cells or cells differentiated therefrom into a mammal exhibiting the disorder. The cells may be either autologous or heterologous. In one embodiment the cells are implanted by systemic injection into a mammal, and in another by directly injecting the cells into an organ of the mammal. Preferred organs or tissues are brain, liver or cardiovascular tissue. Preferred disorders are Alzheimer's, Parkinson's, age-related memory loss, hair loss, burns, aged skin, and skin replacement.

MODES OF CARRYING OUT THE INVENTION

In one aspect, the invention is directed to isolated hair follicle stem cells. It has been found that hair follicle cells express a marker, such as nestin, for central nervous progenitor cells. Thus, in one aspect of the invention, these hair follicle cells are isolated based on the expression of the marker, nestin.

Nestin is an intermediate filament that is a marker for central nervous system progenitor cells. In particular, transgenic mice with green fluorescent protein (GFP) under the control of the nestin regulatory sequences have been generated and used for visualization of the self-renewal and multipotency of CNS stem cells. Although, in a preferred embodiment, the nestin may be linked to a detection agent such as green fluorescent protein to facilitate the isolation process, it is contemplated that other markers for these cells can be used to isolate the hair follicle stem cells as well any other detectable agents. For example, cells can be assayed in vitro or in situ and tested for a labeled binding partner, antibody, or nucleic acid that binds. In embodiments where the hair follicle stem cell is attached to a solid support, assays may employ other types of signal molecules, where unbound signal molecule can be separated from signal molecule bound to the cell. For example, a signal molecule may be labeled with a radioactive isotope (e.g., $^{125}$I, $^{131}$I, $^{35}$S, $^{32}$P, $^{14}$C, or $^{3}$H); a light scattering label (Genicon Sciences Corporation, San Diego, Calif. and see, e.g., U.S. Pat. No. 6,214,560); an enzymatic or protein label (e.g., GFP or peroxidase); or another chromogenic label or dye (e.g., Texas Red). In addition, FACS or other cell sorting mechanism may be used to isolate cells.

Figure 1:
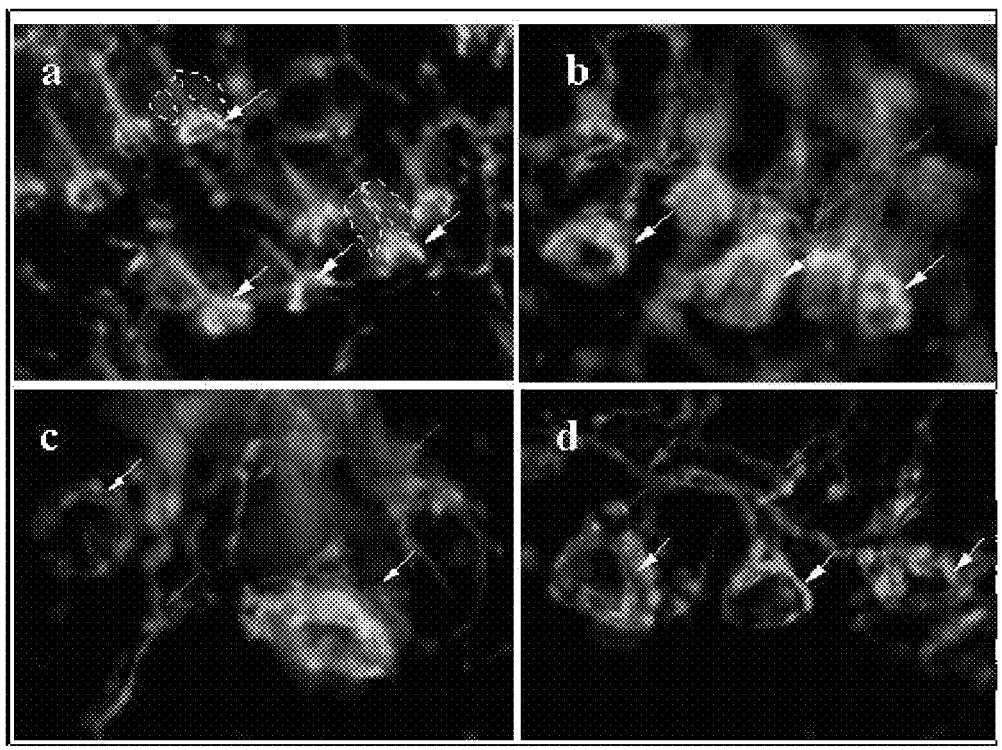
FIG. 1a-d: Hair follicle nestin-GFP expression cells in the telogen phase of nestin-GFP transgenic mouse skin. The skin sample was prepared freshly right after excising out from the back skin of the nestin-GFP transgenic mouse. The sample of the skin was then directly observed by fluorescent microscopy or by confocal microscopy with the dermis side up after dissection out of the subcutaneous tissue. (a, b & c) are images of fluorescent microscopy. (d) is the image of confocal microscopy. Note the unique bell-like structure and location of hair follicle nestin-GFP expressing cells (white arrows) in each hair follicle. The hair follicle nestin-GFP-expressing cells are strictly located right below the sebaceous glands (FIG. 1a, white broken line-out), which is identical to the hair follicle stem cells located and so called as the hair follicle bulge area. Note that the nestin-GFP expressing cells in the hair follicles are connected to each other with a nestin-GFP-expressing nerve-like cell network (gray arrows). Magnifications: a 100×, b & c 200×, d 400×.
Figure 2:
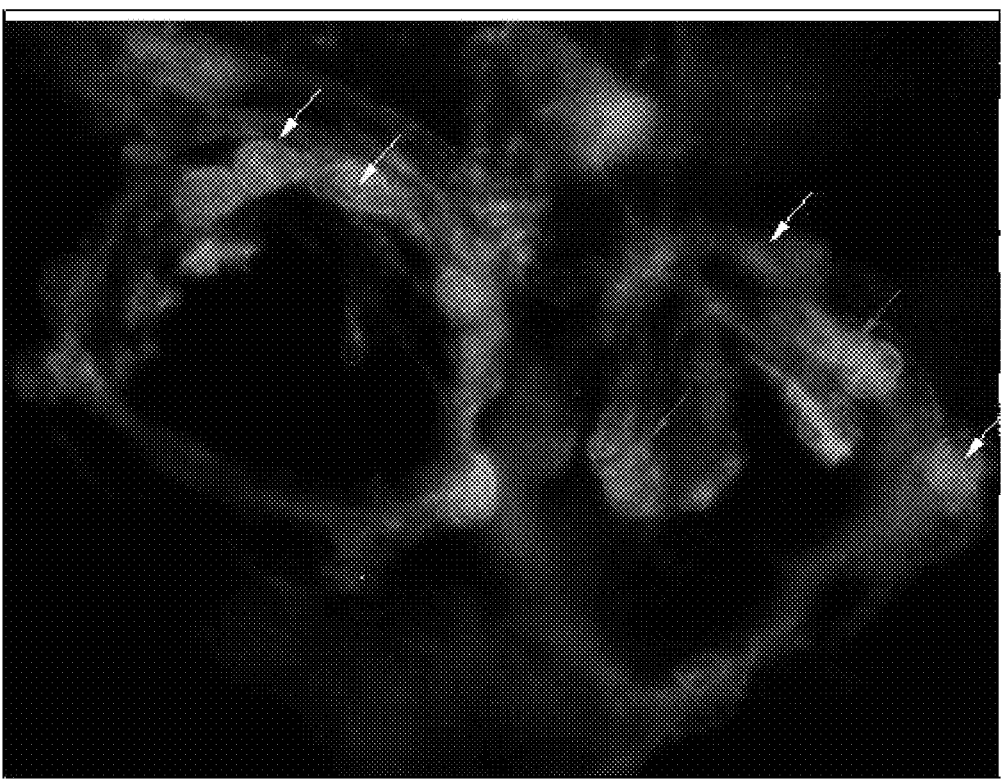
FIG. 2: Hair follicle stem cells forming nascent hair follicle. GFP-expressing hair follicle stem cells in the telogen phase (white arrows). GFP hair follicle stem cells form early anagen new hair follicle (gray arrows). Original magnification 400×.
Figure 3:
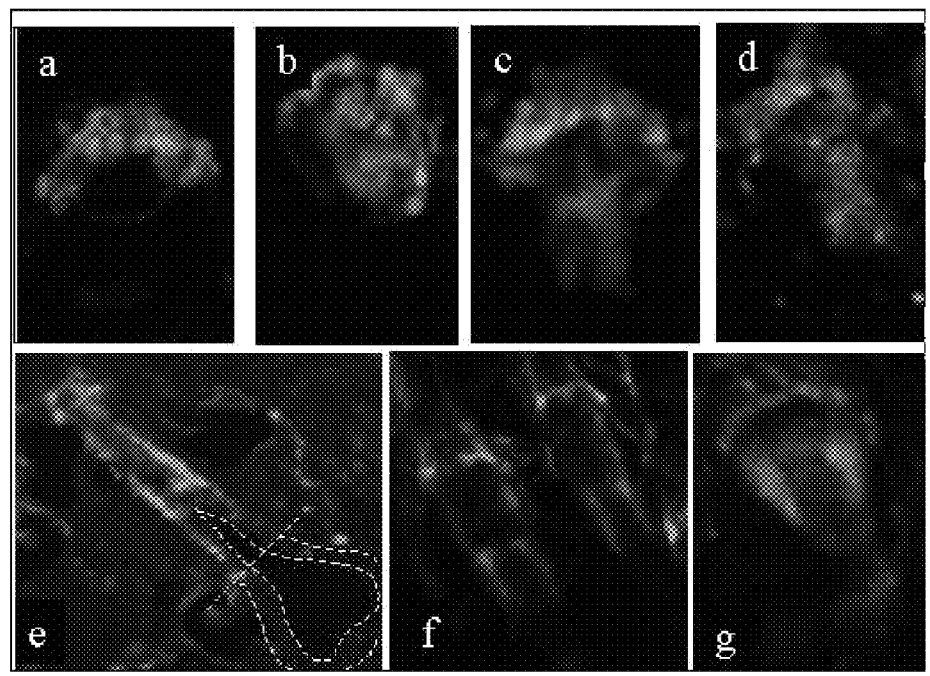
FIG. 3a-f: Confocal images show new hair follicle growing out from the bulge nestin-GFP expression cells and developing through the hair cycle. Anagen hair follicle was introduced by depilation by hot wax on the dorsal skin of 6-7 weeks-old C57B16 nestin-GFP transgenic mice with the hair cycle in telogen determined by the pink skin. (a) is the sample at the time just before depilation and shows the bulge nestin-GFP cells exclusively located in the bulge area. (b) is the day 2 sample after depilation. Note the new hair follicle bud with nestin-GFP expression was just formed directly from the bulge nestin-GFP stem cells. (c & d) are day 4 and 5 samples after depilation and showing the early anagen hair follicle. Note the new hair follicles continued to growing and developing with the expression of nestin-GFP. (e) is the day 8 sample after depilation and showing the middle anagen hair follicle. Note the fully formed hair follicle with nestin-GFP expression in the upper outer-root sheath and no nestin-GFP expression in the hair follicle bulb. (f & g) are day 19-20 samples after depilation and showing the catagen hair follicles. Note that the hair follicles have been degenerated and regressed back to the hair bulge. Confocal microscopy. Magnification: (a, b, c & d) 400×. (e & f) 100×. (g) 200×.

The location of hair follicle stem cells varies depending on the hair-cycle. In early anagen in nestin-GFP transgenic mice, nestin-expressing cells are located in the permanent upper hair follicle right below the sebaceous glands in the follicle bulge where the hair follicle stem cells are located. The nestin-expressing cells in the bulge area are relatively small, oval shaped and surround the hair shaft with short dendrites connecting them to each other. FIG. 3 shows that the location of the nestin-expressing cells in the hair follicle are hair-cycle dependent. During telogen (Example 1 and FIG. 1) and early anagen, the GFP-positive cells, i.e., nestin-expressing cells, are mainly in the bulge area. In FIG. 2, GFP-expressing hair follicle stem cells are seen in both telogen and early anagen. As the hair follicle stem cells from telogen appear to be the most primitive and are localized, they are preferred for harvesting, although the cells may be harvested from any stage of the hair-cycle.

Figure 4:
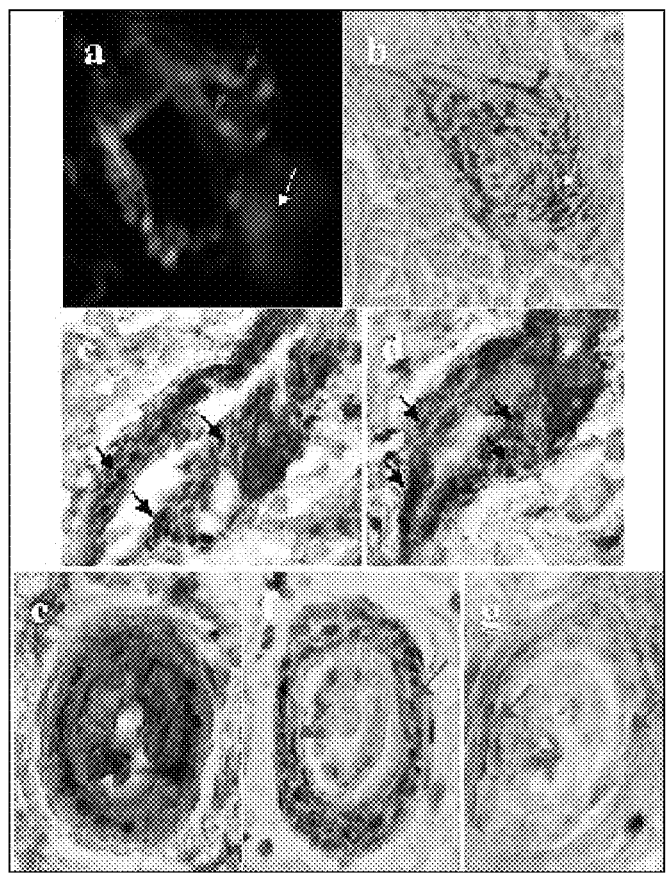
FIG. 4: Co-localization of GFP, nestin and keratin 5/8 & 15 in hair follicle bulge stem cells and outer root sheath cells determined by immunohistochemical staining. (a) is a confocal image of live tissue showing nestin-GFP expressing hair follicle bulge stem cells (gray arrows), which forming the new hair follicle (white arrow). (b) is a paraffin embedded tissue section immunohistochemically stained with nestin antibody (1:100), which showed the exact pattern of nestin expression as nestin-GFP expression in (a). Gray arrows indicate nestin positive hair follicle bulge stem cells. White arrow indicates nestin positive new formed hair follicle. (c) & (d) are two series of paraffin longitudinal sections of nestin-GFP transgenic mouse skin hair follicles and double-immunohistochemical stained with GFP mAb (1:100) and keratin-15 mAb (1:100). GFP is detected by chromogen fast red and keratin-15 is detected by chromogen DAB. Note the localization on nestin-GFP and keratin-15 in the bulge hair follicle stem cells. (e, f, & g) are series of paraffin cross sections of nestin-GFP transgenic mouse skin hair follicles and immunohistochemically stained with GFP mAb (e, 1:100), Keratin 5/8 mAb (f, 1:250) and nestin mAb (g, 1:100) respectively. Note the co-localization of GFP, keratin 5/8 and nestin in the outer root sheath cells of hair follicles. Magnification 400×.
Figure 5:
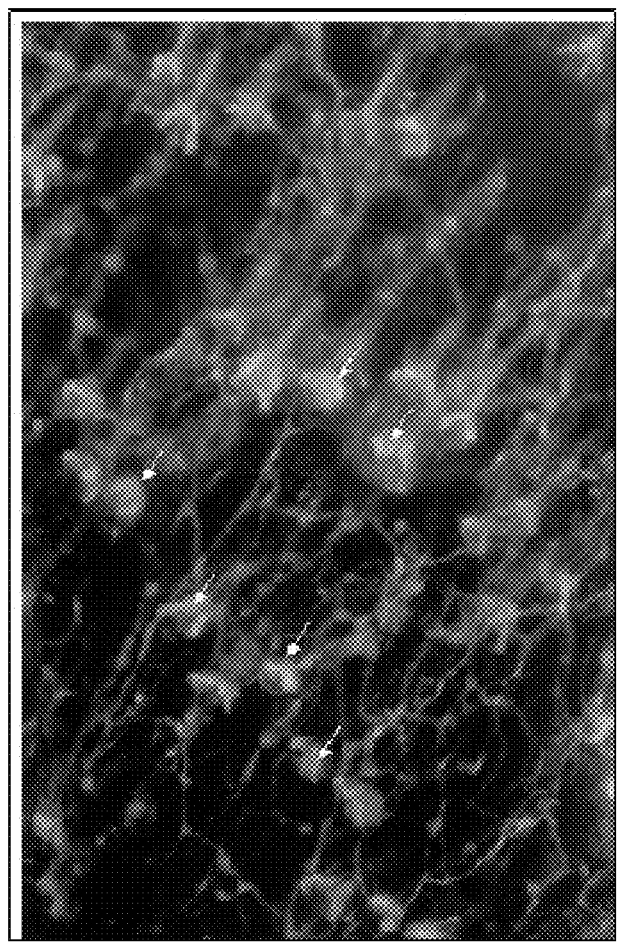
FIG. 5: Hair follicle nestin-GFP-expressing stem cells and interfollicular nerve-like cell network. Telogen phase follicles from the skin of nestin-GFP transgenic mouse skin display GFP-expressing stem cells. Note the unique structure of the stem cells (white arrows) located in the hair follicle bulge area right below the sebaceous glands. The follicles are interconnected with a GFP-expressing nerve-like cell network (gray arrows). Original magnification 100×.

In mid and late anagen, the GFP-expressing cells are located in the upper outer root sheath as well as in the bulge area but not in the hair matrix bulb. These observations suggest that the nestin-expressing cells form the outer-root sheath consistent with behavior observed for hair follicle stem cells. Results of the immunohistochemical staining showed revealed that nestin, GFP, keratin 5/8 and keratin 15 co-localized in the hair follicle bulge cells, outer root sheath cells and basal cells of the sebaceous glands as shown in Example 3 and FIG. 4. These data further demonstrated that nestin-GFP expressing cells in the hair follicle bulge are hair follicle stem cells. Nestin-driven GFP was also found to be highly expressed in an interfollicular neural-like network as shown in FIG. 5. The common expression of nestin in neural stem cells, in hair follicle stem cells, and in an inter-hair-follicle neural-like network suggests their common origin. Example 6 shows the conversion of the nestin-GFP stem cells to neurospheres which differentiate into neuronal cells, astrocytes and possibly other cell types under appropriate conditions as known in the art.

In another aspect, the invention is directed to a method of isolating the hair follicle stem cells comprising providing or excising skin from a mammal and isolating the hair follicle stem cells. Preferably nestin expressing cells from the skin are isolated, thereby isolating hair follicle stem cells. The skin samples may be harvested from any period of the hair-cycle. Preferably, the skin samples are harvested from telogen because it is believed that the hair follicle stem cells preferentially are localized in this stage and thus are easier to harvest. Although not bound by this theory, harvesting cells during telogen also allows the harvest of cells in their most primitive state. As discussed above, however, nestin-expressing cells also are found in anagen, mid-anagen and late anagen. The cells may be isolated using excised skin and separation methods, as in the preferred embodiment, but other methods of isolation are also contemplated. For instance, cells may be harvested from a subject in situ.

These isolated hair follicle stem cells have been found to be pluripotent or multipotential. Thus, in a further aspect of the invention directed to a method of differentiating hair follicle stem cells, the hair follicle stem cells may be cultured under various selected conditions that direct differentiation and provide differentiated cells, such as neurons, astrocytes, smooth muscle cells, or keratinocytes, and adipocytes, among other cells. The culture media for producing neurons may include PDGF or CNTF. The culture media for astrocytes include, for instance, GFAP. In addition, the culture media for smooth muscle tissue include, for instance, FBS. The conditions for differentiating cells discussed in the references below as well as those conditions taught in the art are contemplated in the methods of differentiating cells of the invention.

The implantation can be performed in any manner known in the art. In one embodiment, the hair follicle stem cells or differentiated cells derived therefrom are systemically injected into the subject. In another aspect, the hair follicle stem cells or differentiated cells derived therefrom are injected directly into an organ or tissue of the subject. Preferably the organ or tissue is the brain, liver or an organ or muscle associated with the cardiovascular system, such as the heart. In addition, cells or tissues adhered or grown on synthetic supports which are then implanted are also contemplated. The hair follicle stem cells or differentiated cells derived therefrom can be transplanted heterologously in a different subject than the subject from which the cells were derived. However, due to the accessibility of the hair follicle stem cells, in one preferred embodiment the cells can be obtained from the subject to be treated and if desired, grown to provide differentiated cells, and then either the stem cells or differentiated cells may be transplanted autologously. The use of hair follicle stem cell banks is also contemplated as the stem cells of the invention are sufficiently primitive and thus the host will not likely reject the cells when transplanted.

Many reports (Mezey, E., et al., *Science* (2000) 290:1779-1782; Brazelton, T. R., et al., *Science* (2000) 290:1775-1779; Jiang, Y., et al., *Nature* (2002) 418:41-49; Krause, D. S., et al., *Cell* (2001) 105:369-377; Lagasse, E., et al., *Nat. Med.* (2000) 6:1229-1234; Petersen, B. E., et al., *Science* (1999) 284: 1168-1170; Sata, M., et al., *Nat. Med.*(2002)8:403-409; Shimizu, K., et al., *Nat. Med.* (2001) 7:738-741; Jackson, K. A., et al., *J. Clin. Invest.* (2001) 107:1395-1402; and Orlic. D., et al., *Proc. Natl. Acad. Sci. USA* (2001) 98:10344-10349) have showed the plasticity of adult stem cells derived from various tissues including bone marrow, skin and brain, etc. Mezey, et al., (supra) have shown that transplanted adult bone marrow cells migrated into the brain of mice and differentiated into cells that expressed neuron-specific antigens. Brazelton, et al. (supra), injected marked adult mouse bone marrow into lethally irradiated normal adult mice and subsequently observed donor-derived cells expressing neuronal proteins in the brain. Jiang, et al. (supra), reported that cells co-purifying with mesenchymal stem cells-termed multipotent adult progenitor cells or MAPCs when injected into an early blastocyst, contribute to most, if not all, somatic cell types and differentiate to the hematopoietic lineage, in addition to the epithelium of liver, lung and gut when injected in mice. Krause, et al. (supra), have shown that adult bone marrow cells differentiate into epithelial cells of the liver, lung, GI tract, and skin. Lagasse, et al. (supra), have reported that adult bone marrow cells injected in the FAH (−/−) mouse, an animal model of tyrosinemia type I, restored the biochemical function of its liver.

Petersen, et al. (supra), have shown that injection of the adult marrow cells converted to regenerating hepatic cells. Sata, et al. (supra), have shown that bone-marrow cells give rise to most of the smooth muscle cells (SMCs) that contribute to arterial remodeling mice. Shimizu, et al. (supra), have shown that bone-marrow transplantation of beta-galactosidase—expressing cells into aortic allograft recipients demonstrated that intimal cells included those of marrow origin. Jackson, et al. (supra), found that enriched hematopoietic stem cells differentiated to cardiomyocytes and endothelial cells, and contributed to the formation of functional tissue in mice.

Orlic, et al. (supra), have reported that, in the presence of an acute myocardial infarct, cytokine-mediated translocation of bone marrow cells resulted in a significant degree of myocardium regeneration.

However, Terada, N., et al., *Nature* (2002) 416:542-545, have demonstrated that mouse bone marrow cells can fuse spontaneously with embryonic stem cells in culture in vitro that contains interleukin-3. Moreover, spontaneously fused bone marrow cells can subsequently adopt the phenotype of the recipient cells, which, might be interpreted differentiation. In addition, recently Wagers, A. J., et al., *Science*, (Sep. 5, 2002) [e-published ahead of print] failed to demonstrate transformation of bone marrow stem cells to other cell types in vivo. Although these results raised concerns of the plasticity of adult stem cells, hair follicle stem cells expressing nestin demonstrate a more primitive differentiation and maintain their multipotentiality.

Thus, it is expected that the hair follicle stem cells will provide similar results as the stem cells reported in the literature above and thus can be used to treat various diseases and conditions as known in the art with respect to stem cells derived from other sources such as embryos, bone marrow, brain and skin. As such, one embodiment of the invention is directed to a method of treating a disorder, preferably a neurological or degenerative disorder, comprising implanting the isolated hair follicle stem cells into a mammal exhibiting the disorder.

It is expected that the injected or transplanted hair follicle stem cells of the invention will, under the appropriate conditions, be able to differentiate into cells that express neuronal proteins in the brain, or cells associated with somatic cell types, hematopoietic tissues, cardiomyocytes, endothelial tissues, myocardium tissue, epithelium of liver, lung, gut, GI tract, smooth muscle tissue, skin, hepatic tissue, arterial and cardiovascular tissue as described in the references above. In one preferred embodiment, the hair follicle stem cells or cells that are differentiated therefrom are used in methods of treating diseases or disorders associated with these organs and/or tissues.

It is expected that the hair follicle stem cells will differentiate in vivo once the cells are implanted and act to repair or regenerate the tissue such as liver tissue, brain tissue, cardiovascular tissue. In another aspect, the hair follicle stem cells are differentiated in vitro and the differentiated cells may similarly be used to treat a disorder such as a neurological or degenerative disorder. In a more preferred embodiment, the hair follicle stem cells or differentiated cells derived therefrom are used to treat a disorder selected from the group consisting of Alzheimer's, Parkinson's, and age-related memory loss. In addition, the hair follicle stem cells or differentiated cells derived therefrom can be used to treat hair loss or for skin replacement, or to treat conditions related to the epidermis such as burns or aged skin. Further, the diseases or disorders that can be treated with the hair follicle stem cells or differentiated cells derived therefrom relate to cardiovascular disease or liver disease. The treatment of other diseases is contemplated as discussed below in detail.

In addition, the invention contemplates using the expression system to study and treat diseases discussed below in more detail. The invention also contemplates using the stem cells in vitro to determine the effects of various differentiation potential of the hair follicle stem cells.

In addition, to the particular diseases and disorders mentioned above, it is contemplated that the hair follicle stem cells, or differentiated cells derived therefrom, of the invention can be used in stem cell therapy for cellular proliferative and/or differentiative disorders, disorders associated with bone metabolism, cardiovascular disorders, including endothelial cell disorders, liver disorders, or brain disorders, and preferably brain or liver disorders, as described in more detail below.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the term "cancer" (also used interchangeably with the terms, "hyperproliferative" and "neoplastic") refers to cells having the capacity for autonomous growth, i.e., an abnormal state or condition characterized by rapidly proliferating cell growth. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

The hair follicle stem cells, or differentiated cells derived therefrom, of the invention can be used to treat a variety of proliferative disorders. Such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L., Crit Rev. in Oncol./Hemotol. (1991) 11:267-297); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

The hair follicle stem cells, or differentiated cells derived therefrom, of the invention can be used to treat disorders associated with bone metabolism. "Bone metabolism" refers to direct or indirect effects in the formation or degeneration of bone structures, e.g., bone formation, bone resorption, etc., which can ultimately affect the concentrations in serum of calcium and phosphate. This term also includes activities in bone cells, e.g.-osteoclasts and osteoblasts, that can in turn result in bone formation and degeneration. For example, the hair follicle stem cells, or differentiated cells derived therefrom, of the invention can be used to treat different activities of bone-resorbing osteoclasts such as the stimulation of differentiation of monocytes and mononuclear phagocytes into osteoclasts. Accordingly, the hair follicle stem cells, or differentiated cells derived therefrom, of the invention can be used in the production of bone cells that can influence bone formation and degeneration, and thus can be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

As used herein, disorders involving the heart, or "cardiovascular disease" or a "cardiovascular disorder" includes a disease or disorder which affects the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. A cardiovascular disorder includes, but is not limited to disorders such as arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, valvular disease, atrial fibrillation, long-QT syndrome, congestive heart failure, sinus node dysfunction, angina, heart failure, hypertension, atrial fibrillation, atrial flutter, cardiomyopathiues, e.g., dilated cardiomyopathy or idiopathic cardiomyopathy, myocardial infarction, coronary artery disease, coronary artery spasm, ischemic disease, arrhythmia, and cardiovascular developmental disorders (e.g., arteriovenous malformations, arteriovenous fistulae, raynaud's syndrome, neurogenic thoracic outlet syndrome, causalgia/reflex sympathetic dystrophy, hemangioma, aneurysm, cavernous angioma, aortic valve stenosis, atrial septal defects, atrioventricular canal, coarctation of the aorta, ebsteins anomaly, hypoplastic left heart syndrome, interruption of the aortic arch, mitral valve prolapse, ductus arteriosus, patent foramen ovale, partial anomalous pulmonary venous return, pulmonary atresia with ventricular septal defect, pulmonary atresia without ventricular septal defect, persistence of the fetal circulation, pulmonary valve stenosis, single ventricle, total anomalous pulmonary venous return, transposition of the great vessels, tricuspid atresia, truncus arteriosus, ventricular septal defects). A cardiovascular disease or disorder also includes an endothelial cell disorder.

As used herein, an "endothelial cell disorder" includes a disorder characterized by aberrant, unregulated, or unwanted endothelial cell activity, e.g., proliferation, migration, angiogenesis, or vascularization; or aberrant expression of cell surface adhesion molecules or genes associated with angiogenesis, e.g., TIE-2, FLT and FLK. Endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

Disorders which can be treated by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used to treat hepatic injury, such as portal hypertension or hepatic fibrosis.

In addition, the methods can be employed to treat liver fibrosis attributed to inborn errors of metabolism, for example, fibrosis resulting from a storage disorder such as Gaucher's disease (lipid abnormalities) or a glycogen storage disease, A 1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein can be useful for the treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicella-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin B1) deficiency and vitamin B12 deficiency, neurologic sequelae of metabolic disturbances, including hypoglycemia, hyperglycemia, and hepatic encephalopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

The following examples are intended to illustrate but not to limit the invention.

EXAMPLE 1

Observation of Telogen Phase Nestin-Expressing Cells

Nestin is an intermediate filament (IF) gene that is a marker for central nervous system (CNS) progenitor cells and neuroepithelial stem cells (Lendahl, U., et al., *Cell* (1990) 60:585-596). Nestin-EGFP transgenic mice carrying enhanced green fluorescent protein (EGFP) under the control of the nestin second-intron enhancer have been used for studying and visualization of the self-renewal and multipotency of CNS stem cells (Lendahl, et al., (supra); Zimmerman, L., et al., *Neuron* (1994) 12:11-24; and Kawaguchi, A., *Molecular and Cellular Neuroscience* (2001) 259-273). We observed in the nestin-EGFP mice strong expression of nestin in the hair follicle stem cells as well as in an interfollicular neural-like network.

Nestin-GFP skin samples in telogen phase were directly observed with dermis up and epidermis down under a Nikon-fluorescent microscope equipped with fluorescence optics. Confocal microscopy with an MRC-600 confocal imaging system (Bio-Rad) mounted on a Nikon Optiphot using a 10× PlanApo objective was also used to observe these skin specimens. The nestin-expressing cells were found exclusively and prominently located in the permanent upper part of telogen hair follicles right below the sebaceous glands and in the bulge area (FIG. 1). These cells are relatively small, spindle, oval or round-shaped (FIG. 2).

EXAMPLE 2

Comparison of Nestin-Expressing Cells During Hair-Cycle

We observed that the location of the nestin-expressing cells is hair-cycle dependent. In order to determine how these nestin-GFP-expressing cells are related to the developing hair follicle, 7-8 week old mice in telogen were induced to anagen by depilation. Skin samples (5×5 mm$^2$) were excised from the dorsal skin just before depilation (telogen) as well as on days 1, 2, 3, 4 & 5 (early anagen), days 8 & 10 (middle anagen), days 15 & 16 (late anagen), and days 19 & 20 (catagen), after depilation. As mentioned above, during telogen, the nestin-expressing cells in the hair follicle are located only at the upper permanent bulge region. When the new hair cycle was induced, anagen hair follicles began to grow. Two-to-three days after depilation, new nestin-expressing hair follicle cells proliferated directly from the nestin-GFP-expressing cells located in the bulge. With the hair cycle in middle and late anagen phase, the nestin-expressing hair follicle cells are specifically located in the upper two-thirds of the outer root sheath without expression in the lower one-third of the follicle or hair matrix bulb. The nestin-expressing outer root sheath cells are visualized during the entire anagen and catagen phase. In catagen, when hair bulb matrix cells are undergoing regression and degeneration, the outer root sheath nestin-GFP expressing cells remain and then decrease along with the shrinkage of the hair follicle and eventually are found only in the bulge by the time of the new telogen (FIG. 3).

The dynamic cyclic pattern of the bulge nestin-GFP-expressing cells in the hair cycle strongly indicates they are hair follicle stem cells and provide the first direct evidence of living stem cells forming the new hair follicle structure. Our observations demonstrate that bulge cells actually form the structure of the follicle by following nestin-GFP expressing cells during the hair cycle. Our results are strongly supported by the findings of others. Recently, Oshima, et al., (supra), reported that the upper region of the outer root sheath of vibrissal follicles of adult mice contains multipotent stem cells that respond to morphogenic signals to generate multiple hair follicles, sebaceous glands, and epidermis. These findings correlate with our observations of nestin-GFP-expression in the outer root sheath.

EXAMPLE 3

Further Characterization of Nestin-Expressing Hair Follicle Stem Cells

In order to further characterize these nestin-GFP expressing hair follicle stem cells, co-localization of nestin (1:80, Rat401, DSHB, University of Iowa, Iowa City, Iowa); GFP (1:100, Boehringer Mannheim); keratin ⅝ (1:250, Chemico International, Temecula, Calif.); and keratin 15 one of the potential markers of hair follicle stem cells (1:100, Chemico International, Temecula, Calif.) was determined immunohistochemically in paraffin embedded wild type C57B16 and nestin-GFP transgenic mouse skin. The DAKO ARK animal research kit or DAKO EnVision Doublestain System along with chromogens DAB (3, 3 diaminobenzidine) or nuclear fast red were used for the immunohistochemical staining. Results of the immunohistochemical staining (FIG. 4) revealed that nestin, GFP, and keratin ⅝ and keratin 15 co-localized in the hair follicle bulge cells, outer root sheath cells and basal cells of the sebaceous glands. These data further demonstrated that nestin-GFP expressing cells in the hair follicle bulge are hair follicle stem cells.

We also observed what appears to be a "neural-like" 3-dimensional network of nestin-expressing cells existing in the entire skin layer including epidermis, hair follicle, dermis, subcutaneous and panniculus carnosus interconnecting the hair follicles (FIG. 5). The exact identification and function of these cells need further demonstration. Thus, nestin expression in the hair follicle stem cells and the interfollicular neural-like network suggested a relationship to neural stem cells.

EXAMPLE 4

Isolation of Hair Follicle Stem Cells

In order to further identify whether these nestin-GFP expressing hair follicle cells are multipotent stem cells, we isolated the hair follicle bulge nestin-GFP expressing stem cells and cultured them in vitro. Telogen nestin-GFP transgenic mouse skin sample was excised and minced. The minced tissue was then digested with a mixture of trypsin (0.25%), collagenase (0.4%) and dispase (1.0%) at 37° C. for 2 hours. Individual hair follicles with nestin-GFP expressing cells in the bulge area were isolated under a dissection microscope equipped with fluorescence optics. Then the nestin-GFP expressing cells at the bulge area of hair follicle were further isolated with a fine syringe under the fluorescence dissection microscope.

EXAMPLE 5

Growing Stem Cells

The nestin-GFP expressing cells from the bulge area of hair follicle were transferred to M21 media without growth factor supplements, which is the typical neural maintenance media to grow neurospheres (Uchida, N., et al., *Proc. Natl. Acad. Sci. USA* (2000) 97:14720-14725). After 12 days, neurosphere-like colonies were apparent. In another experiment, isolated nestin-GFP expressing cells from the hair follicle bulge area were grown at 10 cells/mm² in methylcellulose (1.2%) containing neural stem cell culture media supplemented with epidermal growth factor (EGF) (20 ng/ml), fibroblast growth factor (FGF) (20 ng/ml) and leukemia inhibitory factor (Lif) (10 ng/ml) every two days. When spheres were apparent in the culture medium, they were transferred to a new plate without methylcellulose. Secondary spheres were also generated from the primary spheres. Spheres were then assayed for their differentiation potential.

EXAMPLE 6

Differentiation Culture Assay

Figure 6:
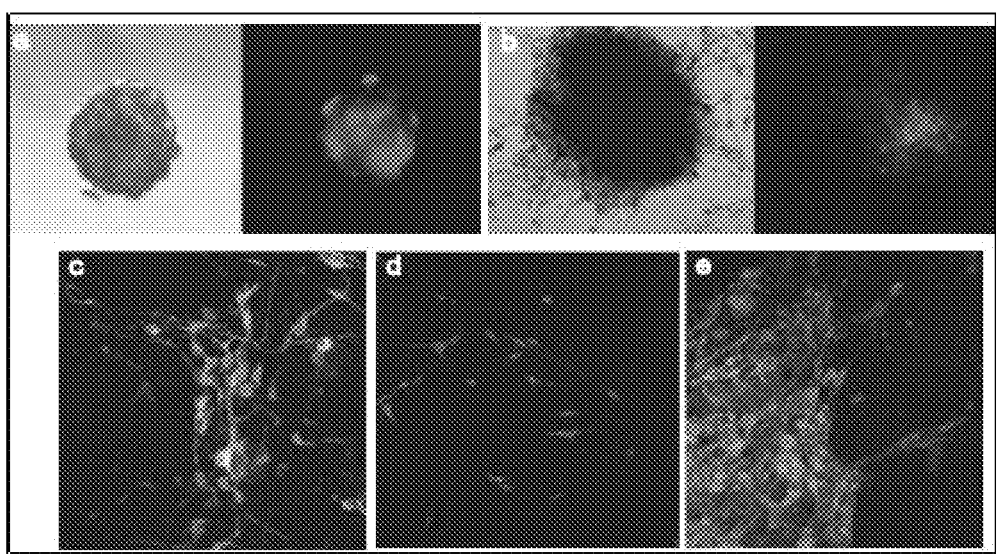
FIG. 6: Nestin-GFP-expressing cells isolated from hair follicles generate multiple cell types in vitro. (a) Neurospheres grown from the hair follicle nestin-GFP-expressing cells. (b) Two days after plating onto coated plates, neurospheres adhere to the surface; cells start migrating away and lose their GFP fluorescence. (c) One week after plating, cells start expressing neuronal marker β-tubulin (fiber-like structure); some cells still express low levels of GFP (bright, relatively circular spots). (d) Two weeks after plating, GABA-positive neuronal cells are evident. (e) One week after plating, cells start expressing astrocytic marker GFAP; some cells still express low levels of GFP.

Spheres were plated onto poly-ornithine/laminin coated plates and cultured in Dulbecco's Modified Eagles Medium (DMEM)-F12 in the presence of fetal bovine serum (FBS) (5%), brain derived neurotrophic factor (BDNF) (10 ng/ml), platelet derived growth factor (PDGF) (10 ng/ml) and ciliary neurotrophic factor (CNTF) (10 ng/ml), respectively. The cells were then analyzed by immunochemical staining with markers for neurons (β-III tubulin, 1:500, Promega); astrocytes (GFAP, 1:300, Sigma); smooth muscle cells (SMA, 1:300, Sigma); and keratinocytes (Pan-keratin, 1:100, Sigma). Adipocytes were determined by visual observation (FIG. 6).

Sphere grown in the presence of BDNF were immunopositive for βIII-tubulin and GABA indicating the presence of neurons. Spheres grown in the presence of PDGF gave rise mostly to neurons, but had occasional GFAP positive cells indicating presence of astrocytes. Cells grown in the presence of CNTF only gave rise to βIII-tubulin positive cells indicating neurons. All spheres grown in the presence of FBS differentiated into smooth muscle actin (SMA) positive cells with occasional keratinocytes.

Based on our observations and experimental data, we conclude here: 1) Nestin-GFP expression demonstrates that bulge cells are the hair follicle stem cells. This is the first demonstration that the bulge cells actually function as stem cells. 2) The fact that hair follicle stem cells express nestin suggested that they are related to neural stem cells. 3) Hair follicles are interconnected by nestin-GFP-expressing neural-like network. 4) Hair follicle stem cells can form multiple cell types including neuronal cells under proper conditions suggesting their potential to form brain cells in vivo.

The invention claimed is:

1. A method to isolate hair follicle stem cells, which method comprises:
   (a) providing individual hair follicles from a mouse or human subject, wherein said hair follicles are in telogen or early anagen phase of the hair cycle;
   (b) obtaining small, spindle, oval or round shaped cells from the permanent upper part of the hair follicles right below the sebaceous glands; and
   (c) identifying the cells as nesting-expressing cells;
   wherein steps (b) and (c) of the method are performed in any sequential order or simultaneously.

2. The method of claim 1, wherein the subject is human.

3. Hair follicle stem cells isolated by the method of claim 1.

* * * * *